(12) United States Patent
Nguyen et al.

(10) Patent No.: US 7,252,661 B2
(45) Date of Patent: Aug. 7, 2007

(54) METHOD AND SYSTEM FOR PATIENT OPTICAL FIXATION

(75) Inventors: Phuoc K. Nguyen, Winter Springs, FL (US); Haizhang Li, Orlando, FL (US); Antonio Rosales, Winter Springs, FL (US)

(73) Assignee: Alcon RefractiveHorizons, Inc., Fort Worth, TX (US)

( * ) Notice: Subject to any disclaimer, the term of this patent is extended or adjusted under 35 U.S.C. 154(b) by 0 days.

(21) Appl. No.: 10/744,329

(22) Filed: Dec. 23, 2003

(65) Prior Publication Data

US 2005/0203492 A1  Sep. 15, 2005

(51) Int. Cl.
*A61F 9/007*  (2006.01)

(52) U.S. Cl. ............................... 606/5; 128/898; 606/4
(58) Field of Classification Search ................ 128/898; 606/4–5
See application file for complete search history.

(56) References Cited

U.S. PATENT DOCUMENTS

| | | | |
|---|---|---|---|
| 4,620,318 A * | 10/1986 | Hill ............................ | 382/117 |
| 4,866,243 A * | 9/1989 | Sakane et al. ......... | 219/121.62 |
| 4,900,145 A * | 2/1990 | Akiyama .................... | 351/221 |
| 4,952,050 A * | 8/1990 | Aizu et al. .................. | 351/221 |
| 5,474,548 A * | 12/1995 | Knopp et al. .................. | 606/4 |
| 5,886,768 A * | 3/1999 | Knopp et al. ................ | 351/212 |
| 5,947,955 A | 9/1999 | Kadambi | |
| 6,004,313 A | 12/1999 | Shimmick | |
| 6,008,941 A * | 12/1999 | Feldman et al. ............ | 359/565 |
| 6,027,216 A | 2/2000 | Guyton | |
| 6,059,773 A * | 5/2000 | Maloney et al. ................ | 606/4 |
| 6,159,202 A | 12/2000 | Sumiya | |
| 6,238,385 B1 | 5/2001 | Harino | |
| 6,338,559 B1 * | 1/2002 | Williams et al. ............ | 351/212 |
| 6,406,473 B1 | 6/2002 | Simmick | |
| 6,411,371 B1 * | 6/2002 | Hinderling et al. ........ | 356/4.01 |
| 6,460,997 B1 | 10/2002 | Frey | |
| 6,491,687 B1 | 12/2002 | Sumiya | |

(Continued)

*Primary Examiner*—Henry M Johnson, III
(74) *Attorney, Agent, or Firm*—Armando Pastrana, Jr.

(57) ABSTRACT

A method and system for patient optical fixation are disclosed. One embodiment of the system comprises: a light source operable to provide a fixation light beam; a filter optically coupled to the light source and operable to attenuate the fixation light beam to provide an apodized light beam, wherein the apodized light beam comprises a more attenuated portion and a less attenuated portion; and a viewer, operable to receive a reflected fine align beam and a reflected coarse align beam from a fixation target. The light source can be, for example, a laser, a light emitting diode or a laser diode. The filter can be a neutral density ("ND") filter, comprising: an aperture through which a first portion of the fixation light beam can pass unattenuated by the ND filter to form the less attenuated portion of the apodized light beam; and a filter region for attenuating a second portion of the fixation light beam to form the more attenuated portion of the apodized light beam. This embodiment of the system of the present invention can further comprise a set of focusing lenses operable to receive and focus the more attenuated portion of the apodized light beam to provide a patient coarse align light beam to aid a patient in achieving fixation on the less attenuated portion of the apodized light beam. The focusing lenses can be configured to provide an intermittent blinking patient coarse align light beam. The fixation target can be a human eye and the selected region can be the cornea of a human eye.

26 Claims, 4 Drawing Sheets

U.S. PATENT DOCUMENTS

| | | |
|---|---|---|
| 2001/0041884 A1* | 11/2001 | Frey et al. .................... 606/5 |
| 2002/0007178 A1 | 1/2002 | Donitzky |
| 2002/0082629 A1 | 6/2002 | Cox |
| 2003/0120266 A1* | 6/2003 | Fujieda ......................... 606/5 |
| 2003/0133102 A1* | 7/2003 | Opsal ....................... 356/237.1 |
| 2003/0137659 A1* | 7/2003 | Milshtein ................. 356/237.2 |
| 2004/0165872 A1* | 8/2004 | Nanjo et al. ................... 396/18 |
| 2004/0246474 A1* | 12/2004 | Guetta et al. ............ 356/237.2 |

* cited by examiner

METHOD AND SYSTEM FOR PATIENT OPTICAL FIXATION

TECHNICAL FIELD OF THE INVENTION

The present invention relates to ophthalmic surgical systems and methods, and, more particularly, to a patient gaze-fixation method and system for use during eye surgery. Even more particularly, the present invention relates to a method and system for patient optical fixation that provides feedback to both the patient and the surgeon for coarse and fine alignment of the patient eye to an optical axis.

BACKGROUND OF THE INVENTION

Eye surgery, and in particular, laser eye surgery procedures such as phototherapeutic keratectomy (PTK), photorefractive keratectomy (PRK), laser-assisted in situ keratomileusis (LASIK), and similar refractive procedures, depend heavily on the precise alignment between the eye and a therapeutic (surgical) laser beam. Known techniques for laser eye surgery procedures typically use an ultraviolet or infrared laser to photo-ablate (remove) a microscopic layer of stroma tissue from a cornea to alter its refractive properties. Refractive errors of the eye can thus be corrected by removing a designated portion of the corneal tissue with the laser. Laser ablation procedures can be used to remove targeted portions of the cornea to shape the cornea's contour and correct various conditions, such as myopia, astigmatism, hyperopia and other refractive errors of an eye.

Typical laser eye surgery devices require a patient to be awake during a procedure. This is because a conscious patient can help to improve the outcome of the procedure by maintaining an alignment between his or her eye and the beam of the therapeutic laser. The ability of the patient to maintain such an alignment between his or her eye and the therapeutic laser beam is greatly enhanced by having the patient focus on a target during the procedure.

Such a fixation target can be provided by a commercially available laser light source. Existing commercial laser fixation devices typically use a simple laser beam focused on or near the patient's cornea and rely on the scattered beam image on the cornea to provide alignment These prior art fixation devices use powerful lasers potentially exceeding the limit for a Class 1 laser.

Other prior art fixation devices use a point light source, which expands spatially by the time it reaches a patient's eye. For these devices, separate fixation targets are required for angular and lateral alignment of the eye. Furthermore, the fixation image on the retina becomes blurry due to the patient's refractive (dioptric) errors and the large light bundle that hits the cornea.

Prior art fixation devices, however, have several limitations. The powerful lasers used by prior art fixation systems are, at best, uncomfortable for a patient and, at worst, can damage a patient's retina. This is because the patient fixes his or her gaze on the high power fixation laser throughout the surgery, which causes a very strong stimulus on the macular portion of the retina of the eye undergoing surgery. Thus, although the high power laser provides for the reflection which allows the surgeon to align the patient's visual axis, the potential for permanent eye damage and the lack of patient comfort are of great concern. Furthermore, prior art fixation systems do not provide an effective range of both coarse and fine alignment to allow the patient and the surgeon to easily determine and correct the degree of misalignment between the patient eye and the therapeutic laser beam path.

Therefore, a need exists for a method and system for patient optical fixation that can reduce or eliminate the problems associated with prior art fixation methods and systems. Such a method and system can significantly enhance the ease of use for both the surgeon and the patient via coarse and fine alignment feedback, the use of efficient lower-intensity lasers, and the significantly improved patient fixation, regardless of a patient's dioptric error. A surgeon can thus accurately and efficiently monitor the spatial alignment of a patient's eye, as well as the patient's gaze direction.

BRIEF SUMMARY OF THE INVENTION

The embodiments of the method and system for patient optical fixation of the present invention substantially meet these needs and others. One embodiment of the system for patient optical fixation comprises: a light source operable to provide a fixation light beam; a filter optically coupled to the light source and operable to attenuate the fixation light beam to provide an apodized light beam, wherein the apodized light beam comprises a more attenuated portion and a less attenuated portion; and a viewer, operable to receive a reflected fine align beam and a reflected coarse align beam from a fixation target. The system can further comprise a wavefront analyzer, as known to those familiar with the art, for determining an ablation profile for the fixation target.

The light source can be, for example, a laser, a light emitting diode or a laser diode. The light source can further comprise: a fine align light source operable to provide a fine align light beam; and a coarse align light source operable to provide a coarse align light beam, wherein the fine align light source frequency is different from the frequency of the coarse align light source, and wherein the more attenuated portion of the apodized light beam comprises the filter-attenuated coarse align light beam, and the less attenuated portion of the apodized light beam comprises the filter-attenuated fine align light beam. The filter can be a neutral density ("ND") filter, comprising: an aperture through which a first portion of the fixation light beam can pass unattenuated by the ND filter to form the less attenuated portion of the apodized light beam; and a filter region for attenuating a second portion of the fixation light beam to form the more attenuated portion of the apodized light beam.

The ND filter aperture can be a circular aperture, and the less attenuated portion of the apodized light beam can be approximately a central circular region of the apodized light beam and the more attenuated portion of the apodized light beam can be approximately an annular outer region of the apodized light beam. Further, the inner diameter of the more attenuated portion can be approximately equal to the diameter of the less attenuated portion. This embodiment of the system of the present invention can further comprise a set of focusing lenses operable to receive and focus the more attenuated portion of the apodized light beam to provide a patient coarse align light beam to aid a patient in achieving fixation on the less attenuated portion of the apodized light beam. The focusing lenses can be configured to provide an intermittent blinking patient coarse align light beam.

The fixation target can be a human eye and the selected region can be the cornea of a human eye. The system can further comprise a beam splitter for redirecting a reflected portion of the apodized light beam, comprising an image of the fixation target, to the viewer, wherein the viewer is offset from the fixation light beam optical axis. The viewer can be, for example, a video camera, operable to transmit the image of the fixation target to a monitoring device, or a microscope. The present invention can thus provide the means for a doctor to monitor the spatial positioning and/or the angular alignment of a patient's eye via the Purkinje image of a narrow beam laser.

Further embodiments of the present invention can include a method for patient optical fixation in accordance with the teachings of this invention. One embodiment of the method can comprise the steps of: providing a fixation light beam; attenuating the fixation light beam to provide an apodized light beam, wherein the apodized light beam comprises a more attenuated portion and a less attenuated portion; directing the apodized light beam onto a fixation target to produce a reflected fine align beam and a reflected coarse align beam; receiving the reflected fine align beam and the reflected coarse align beam at a viewer; and adjusting the fixation target position relative to the apodized light beam axis based on the reflected fine align beam and the reflected coarse align beam. The method can further comprise aligning the fixation target with the apodized light beam axis and focusing the more attenuated portion of the apodized light beam to provide a patient coarse align light beam to aid a patient in achieving fixation on the less attenuated portion of the apodized light beam.

Embodiments of the method and system of this invention can be implemented within any ophthalmic surgical environment, and in particular can be implemented within a refractive surgery environment. For example, the embodiments of this invention can be implemented within the LadarVision™ System manufactured and sold by Alcon Laboratories, Inc. of Fort Worth, Tex. Embodiments of this invention can thus be incorporated within a surgical machine or system for use in refractive or other eye surgery. Other uses for a method and system for patient optical fixation in accordance with the teachings of this invention will be known to those familiar with the art and are contemplated to be within the spirit and scope of the present invention.

BRIEF DESCRIPTION OF THE SEVERAL VIEWS OF THE DRAWINGS

A more complete understanding of the present invention and the advantages thereof may be acquired by referring to the following description taken in conjunction with the accompanying drawings in which like reference numbers indicate like features and wherein.

DETAILED DESCRIPTION OF THE INVENTION

Figure 1A:
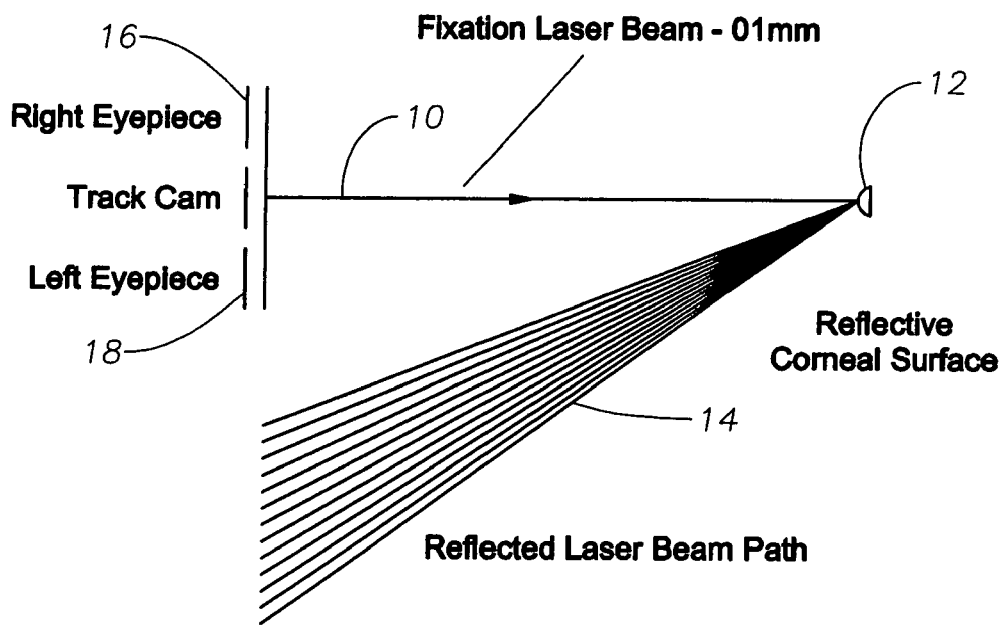
FIGS. 1A and 1B illustrate the Purkinje Image principle as used for providing alignment feedback.

Preferred embodiments of the present invention are illustrated in the FIGURES like numerals being used to refer to like and corresponding parts of the various drawings.

The various embodiments of the present invention provide a method and system for patient optical fixation for use in ophthalmic surgical procedures, such as refractive laser eye surgery. Embodiments of the method and system of the present invention can comprise a nearly collimated laser light source as a fixation light, such that the laser beam intensity and the spot size on a patient's retina will not change appreciably with dioptric error of the patient's eye, and such that the light image on the retina is minimally affected by the LASIK flap cut and the on-going laser surgery. The fixation light system of this invention incorporates features to provide a surgeon feedback for coarse and fine alignment adjustment of the patient's eye with a therapeutic laser light source. Coarse and fine alignment feedback for the surgeon using the specular reflection of the fixation light source on the patient's cornea can, in accordance with the teachings of this invention, be implemented using a strategized beam profile such that the monitored fixation light beam intensity is correlated to the distance between the corneal apex and the center of the fixation light beam. The strategized beam can be effected by means of intensity modification (apodization) or by means of phase modification (e.g., via phase plates and/or lenses). Examples of a strategized beam profile of the method and system of this invention include, but are not limited to, the example illustrated in FIG. 2.

Embodiments of the method and system of this invention provide a surgeon the ability to effectuate coarse alignment of the patient eye with a therapeutic laser using a strategized beam image reflected from the patient's cornea. When a fixation light of the embodiments of this invention is used in this mode, the image from a patient's cornea can be superimposed onto a brighter specular reflection near the corneal apex. The specular reflection viewed through a surgical microscope or a camera system provides the surgeon feedback for fine alignment. Embodiments of the fixation system of the present invention can also comprise features to provide a patient feedback for coarse and fine alignment. Coarse and fine alignment feedback for the patient are likewise provided by the strategized beam profile, such that the beam intensity at the patient retina is correlated to the lateral separation between the corneal apex and the center of the fixation light beam, optical path. Examples of the strategized beam profile as seen from the patient's point of view can include, but are not limited, to that illustrated in FIG. 3. The coarse alignment light source and the fine alignment light source can be of the same frequency (i.e., color) for design efficiency, or they can be of different frequencies to optimize patient ease of use.

Unlike the prior art, the embodiments of the method and system of this invention use a low-power laser beam as a fixation light source (e.g., a Class 1 laser or lower). Embodiments of this invention do, however, take advantage of the Purkinje Image principal for alignment feedback. If a light is held in front of a person, an external observer looking into the person's eyeball will see the reflection of the light in the person's eyeball. The point on the eye at which the reflection is seen by the external observer identifies, with fair accuracy, the corneal apex. The embodiments of this invention use the Purkinje Image principle in that the return from the eye of the fixation light source will increase in intensity the closer that the fixation light beam is to impinging on the corneal apex.

Figure 1B:
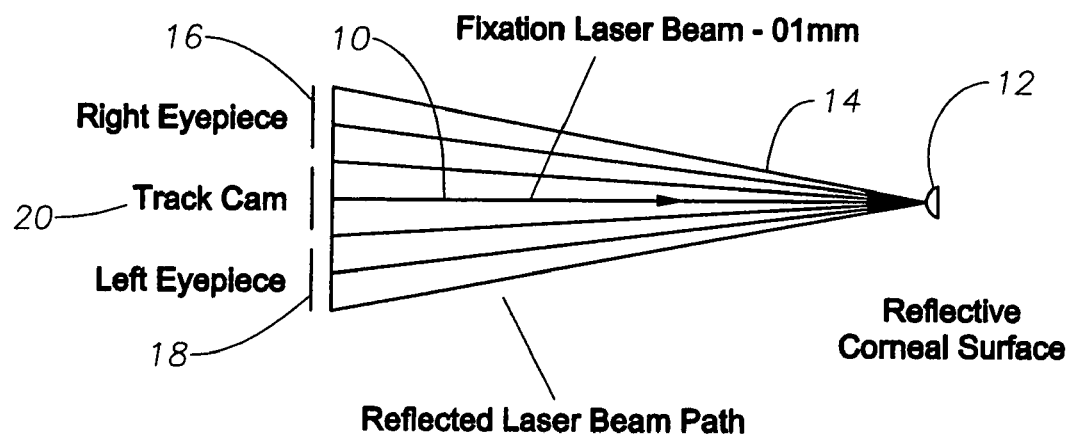

FIGS. 1A and 1B illustrate the principle behind the Purkinje Image. FIG. 1A shows a fixation laser beam 10 focused on a reflective corneal surface 12, but offset from the corneal apex by 2 mm. In this example, the reflected laser beam path 14 provides a reflection of fixation laser beam 10 which is not visible to a surgeon viewing the eye through left or right binocular eyepieces 16 and 18. Because the fixation laser beam 10 is not focused on the corneal apex, the reflected laser beam path 14 is not visible to the surgeon and the surgeon knows that he or she must adjust the alignment between the fixation laser beam 10 and the patient's cornea (i.e., the alignment between the patient eye and a therapeutic laser) prior to performing the surgical procedure.

In contrast, FIG. 1B shows the same fixation laser beam 10 focused on the corneal apex of reflective corneal surface 12. As can be seen from FIG. 1B, a surgeon viewing a patient's eye through left and right eyepieces 16 and 18 of a surgical microscope will see a return along reflected laser beam path 14 of fixation laser beam 10 and will be able to determine that the patient's eye is properly aligned with the optical path of a therapeutic laser beam (i.e., the same optical path as fixation laser beam 10). Also illustrated in FIGS. 1A and 1B is that the fixation laser beam spot size must be chosen to encompass the surgical binocular 16 and 18 apertures, and/or the track camera 20 aperture. The laser beam size is chosen to obtain an effective balance between accuracy and sensitivity. This balance is a subjective measure and can be based on experience with surgeon preferences. The embodiments of the method and system for patient optical fixation of the present invention comprise a fixation laser beam having a laser beam spot size on the order of about 1 mm in diameter, and related mechanisms that can provide a surgeon the ability to more easily and accurately align (fixate) a patient eye to a therapeutic laser and to continuously monitor the patient's fixation.

Figure 2:
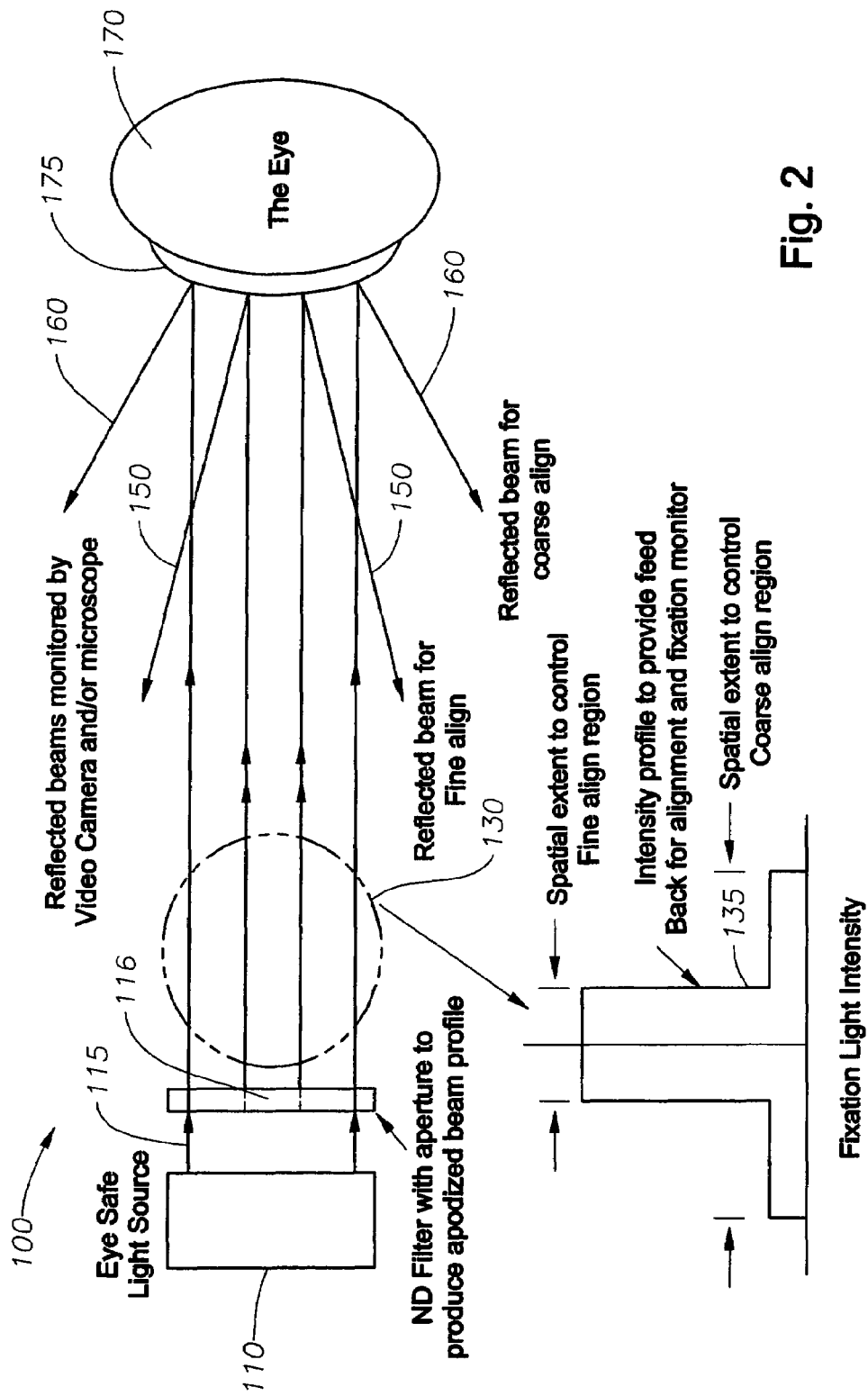
FIG. 2 illustrates one embodiment of a system for patient optical fixation in accordance with this invention.

FIG. 2 is a simplified block diagram illustrating one embodiment of the system for patient optical fixation of the present invention. Optical fixation system 100 comprises a light source 110 optically coupled to an ND (neutral density) filter 120. Light source 110 provides a nearly collimated beam of light 115 that impinges upon neutral density filter 120. Light source 110 can be reasonably small in the lateral extent and the nearly collimated nature of the light it provides improves the accuracy of the patient-to-therapeutic-laser alignment. Light source 110 can be a laser, a light emitting diode (LED), or a laser diode as know to those familiar with the art. Neutral density filter 120 further comprises an opening (aperture) 116 (which can be of various shapes and/or sizes) through which it can pass an unattenuated portion of light beam 115. As shown in FIG. 2, neutral density filter 120 attenuates an outer diameter of the light beam 115 from light source 110, while passing a central region of light beam 115 unattenuated through the opening 116 in its center. After passing through neutral density filter 120, light beam 115 emerges as attenuated beam 130, having an intensity profile 135.

As can be seen from intensity profile 135, the central portion of attenuated beam 130 has a greater intensity than the outer diameter portions and serves to provide a fine align reflected beam 150 (fine adjustment) to aid in alignment of the patient fixation. The intensity profile 135 of attenuated beam 130 serves to provide feedback for aligning and monitoring a patient's fixation. The outer region of attenuated light beam 130 provides a less intense light to aid in coarse alignment of the patient's eye fixation. Neutral density filter 120 provides one way to apodize (strategize) the light beam 115 profile. However, as will be familiar to those of average skill in the art, there are many other ways to apodize a beam profile, such as by using multiple filters, fresnel lenses, and/or different types of lens coatings. The use of such ways to apodize a beam profile are contemplated to be within the scope of this invention. For example. neutral density filter 120 can comprise a fresnel lens or lenses.

Attenuated beam 130 impinges upon cornea 175 of a patient eye 170. Cornea 175 reflects attenuated beam 130 in the form of reflected fine align beam 150 and reflected coarse align beam 160. Reflected fine align beam 150 is the reflected center portion of attenuated beam 130 and is of a greater brightness (intensity) than reflected coarse align beam 160, which is the reflected outer portion of attenuated beam 130.

A surgeon can align a patient's eye with the optical path of a therapeutic laser using the varying intensities of the reflected fine align beam 150 and reflected coarse align beam 160. FIG. 2 illustrates how the embodiments of the system and method of this invention can provide a surgeon feedback for purposes of obtaining patient eye fixation. If the corneal apex of the patient cornea 175 is within the range of the central region of attenuated beam 130 (the fine alignment region), the surgeon will see a strong (bright) reflection from the cornea 175. The surgeon will then know that the fixation light beam center is incident on the patient's eye near the corneal apex, and that he or she can make smaller adjustments than if the fixation light beam (attenuated beam 130) center were further out from the corneal apex. On the other hand, if the corneal apex is illuminated by the outer regions of the attenuated beam 130, a dimmer reflection will be provided to the surgeon and the surgeon will know that the patient's corneal apex is further out of line with the optical axis of a therapeutic laser (i.e., the fixation light source) and that he or she can make relatively coarse (larger) adjustments. If the surgeon sees no reflection of attenuated beam 130 from the patient cornea 175, then he or she will know that the corneal apex is outside of the path of attenuated beam 130 all together and that he or she must make a larger correction still to get proper patient fixation.

The apodized/strategized beam profile 135 of attenuated beam 130 of the present invention can thus be used to optimize the accuracy of patient eye fixation alignment while minimizing sensitivity. Therefore, ease of use with high accuracy in patient fixation can be achieved. Note that a typical spot size of the fine alignment beam profile (the unattenuated portion of light beam 115) of attenuated beam 130 is on the order of about 1 to 2 mm. The coarse alignment beam profile (the attenuated portion of light beam 115) of attenuated beam 130 is typically on the order of about 4 or 5 mm from the center of attenuated beam 130.

Figure 3:
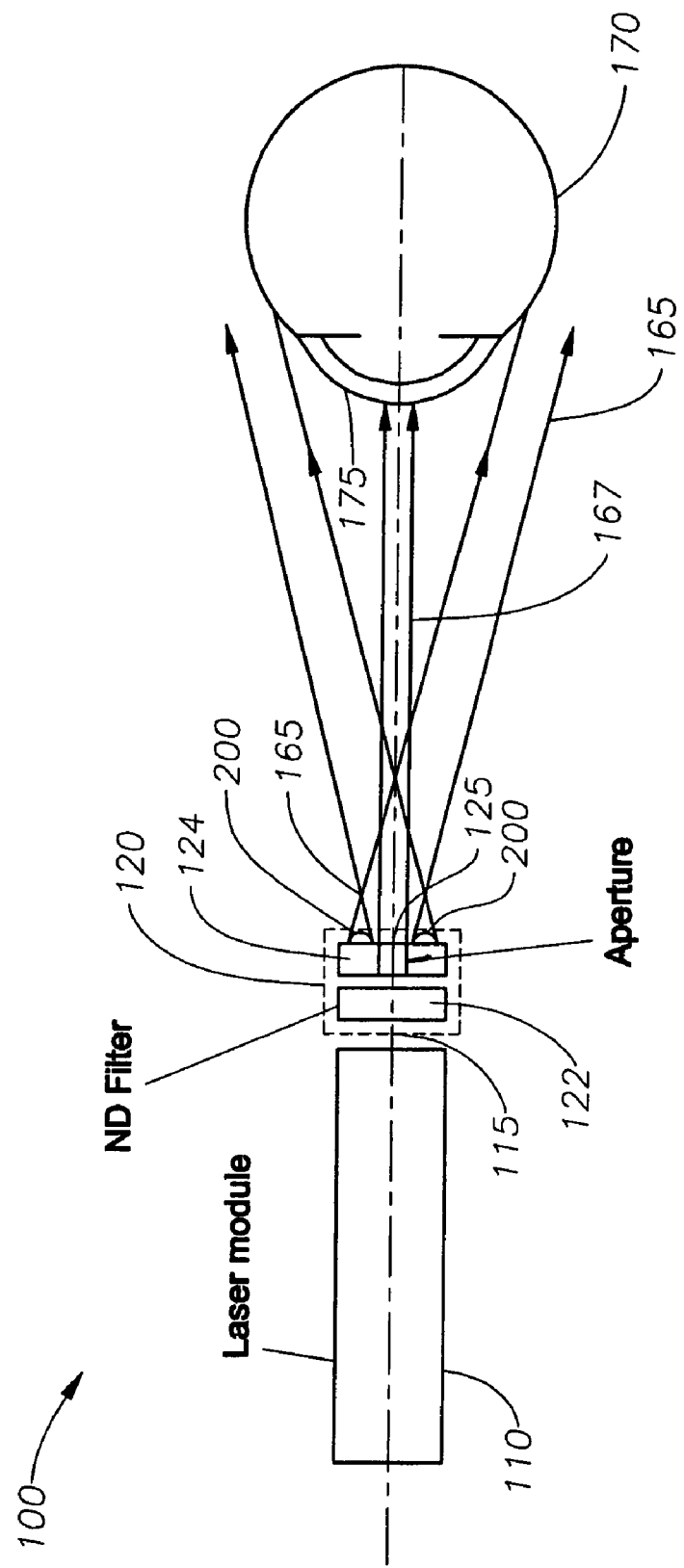
FIG. 3 is a simplified block diagram of an embodiment of the system for patient optical fixation of this invention illustrating operation as seen from a patient's perspective.

FIG. 3 is a simplified block diagram of one embodiment of the system for patient optical fixation of this invention illustrating the view from a patient's perspective. Light source 110, which can comprise a Class 1 laser module, provides a light beam 115 to ND filter 120. The embodiment of ND filter 120 shown in FIG. 3 comprises two separate ND filters, a first ND filter 124 having no aperture, and a second ND filter 124 downstream along the optical path from the first ND filter 122 and having an aperture 125. This combination ND filter 120 can be used to provide attenuated beam 130 and fixation light intensity profile 135 as previously discussed with reference to FIG. 2.

In the embodiment of FIG. 3, system 100 additionally comprises focusing lenses 200 for focusing the attenuated (coarse align) portion of light beam 115 into patient coarse align beams 165. Patient coarse align beams 165 comprise the attenuated portion of light beam 115 that does not pass through aperture 125. Fine align fixation beam 167 comprises the unattenuated portion of light beam 115 that passes through aperture 125.

Focusing lenses 200 provide pilot lights for a patient to guide the patient's gaze to fine align fixation beam 167. Focusing lenses 200 spread the attenuated light 115 outward as coarse align beams 165 that provide the patient a sense of the approximate location of the central fine align fixation beam 167 by providing dimmer, attenuated guiding light beams at the periphery of the fine align fixation beam 167. Thus, if the patient sees one of the fainter beams originating from a focusing lens 200, he or she will know to move his or her head to the left or right to search for the brighter fine align fixation beam 167. The coarse align beams 167 provided through focusing lenses 200 will thus serve to grab the patient's attention and let him or her know that he or she is within range of the main light beam. Coarse align beams 165 originating from different focusing lenses 200 may overlap and will typically encompass a spread of about 1 inch. The various embodiments of the system of the present invention can comprise focusing lenses 200 to aid the patient in obtaining fixation.

A physician performing laser eye surgery on a patient will generally position the patient so that he or she can see the fine align fixation beam 167 and fixate on it. However, if the surgeon does not properly position the patient, the patient will be able to detect a misalignment by seeing the dimmer coarse align beams 165 and adjusting themselves to fixate on fine align fixation beam 167. Once the patient sees the bright fine align fixation beam 167, at its brightest point the patient will know that he or she is properly centered and can fixate on the light beam from light source 110. It should be noted that fine align fixation beam 167, when reflected from the patient's cornea, corresponds to reflected fine align beam 150 from the surgeons perspective of FIG. 2. Similarly, when reflected by the patient's cornea, coarse align beam 165 corresponds to reflected coarse align beam 160 of FIG. 2.

The coarse align beam 165 can comprise, in some embodiments, blinking pilot lights that blink on and off to capture a patient's attention. This can be accomplished, for example, by using a separate light source for the pilot lights or by occluding at intervals the attenuated light leaving focusing lenses 200. In such an embodiment, once the patient is aligned with the fine align fixation beam 167, fine align fixation beam 167 will saturate the patient's retina and the pilot lights will no longer be visible to the patient. Further, the pilot lights (i.e., the coarse align beams 165) can be a different color than the fine align beam 167 to further increase contrast and ease of use in obtaining patient fixation.

Figure 4:
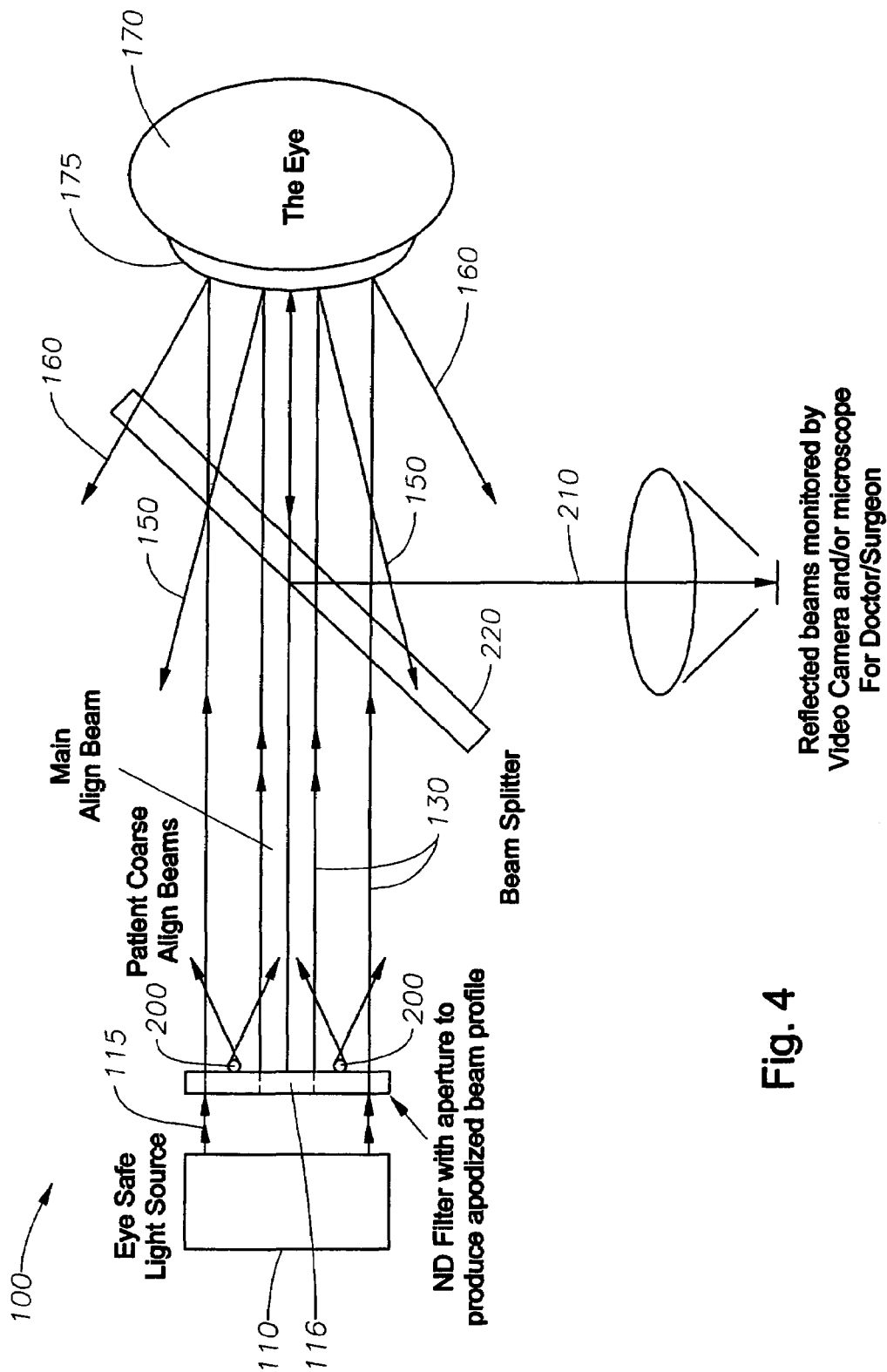
FIG. 4 is a simplified block diagram of an embodiment of the system for patient optical fixation of this invention illustrating the different viewing perspectives available to a surgeon.

FIG. 4 is a simplified block diagram of one embodiment of the system for patient optical fixation of this invention illustrating the different view points available to a surgeon in a typical refractive surgery. FIG. 4 illustrates the capability of the system of the present invention to allow a surgeon to monitor patient fixation, and the surgery, from perspectives other than an in-line perspective. As shown in FIG. 4, reflected beam 210 comprises a reflection of the central portion of attenuated beam 130 of the previous FIGURES. Reflected beam 210 is directed to a video camera and/or a microscope for monitoring by the surgeon or another observer. For example, the reflected beam 210 (and corresponding image) can be provided to a video camera for display on a monitor. Reflected beam 210 is directed to a video camera or other monitoring device by means of a beam splitter 220, as known to those familiar with the art. Beam splitter 220 allows attenuated beam 130 to pass through essentially undisturbed on its way to the eye 170 and then provides a reflected image of the eye in the form of reflected beam 210, by means of its opposite surface. Like numbered elements of FIG. 4 correspond to like numbered elements in FIGS. 3 and 2.

Unlike prior art fixation systems and methods, the various embodiments of the system and method for patient optical fixation of this invention can provide a narrow, nearly collimated fixation beam which significantly reduces the sensitivity of the fixation spot size on the retina due to the patient's dioptric errors. The method and system of this invention provide a much more user friendly fixation beam that significantly enhances ease of use for both the surgeon and the patient via coarse and fine alignment feedback, as illustrated in the FIGURES discussed herein. Further, unlike the prior art, the method and system of this invention provide a laser beam size and profile that is strategized to provide alignment feedback to a surgeon and/or an operator as well as to the patient for fine and coarse fixation alignment. The system of this invention can also comprise a low power light source, such as a Class 1 laser, to achieve efficient and convenient fixation that is more comfortable for the patient. The system of the present invention can thus significantly improve patient visibility and fixation on the fixation light beam.

The strategized profile of the light beam of the embodiments of the system of the present invention has been discussed with reference to a stair-step profile. However, other profiles as known to those familiar with the art are contemplated and intended to be within the true scope and spirit of this invention. For example, Gaussian profiles, triangular profiles, or combinations of such profiles can be used by the present invention. Examples of methods that can be used to create a strategized beam profile include dielectric coatings on the optical substrates, neutral density filters, such as discussed above, spatial light modulators, light valves, diffractive optical elements, fresnel lenses. lenslets and lenslet arrays. These methods are contemplated to be within the scope of this invention. In particular, a dielectric coating for providing a strategized profile can be placed on the transmissive optical substrate or on a reflective optical substrate, and the density of the coating can be varied to obtain the desired strategized profile.

One advantage of a triangular strategized profile is that it can provide a shaded return having an intensity corresponding to the position of the patient with reference to the fixation beam. Thus, the closer the patient gets to the center of the fixation beam, the brighter the fixation beam appears to the patient. This is in contrast to the stair-step strategized profile discussed above, in which the intensity of the beam only informs the patient that he or she is in the fine or coarse region, and does not provide an increasing or decreasing profile as the patient gets closer or further away from the central beam.

The embodiments of the method and system of this invention can thus provide a means to align a reflective curved surface, e.g., an eyeball, with a laser light source for the purposes of performing an ablation procedure on that surface. The importance of being properly centered on the apex of the curved surface of the eyeball cannot be overstated, as it is a primary means of ensuring that the laser is centered on a proper position for the ablation to result in a desired ablation profile. For example, in the case of refractive eye surgery, an error in position of just 0.25 millimeters off of the corneal apex can noticeably affect the performance and results of the surgery. It is thus important that the patient properly fixate to avoid ablation of the wrong portions of the cornea. Although laser ablation systems can be combined with a tracking system, which can typically compensate for a few millimeters of movement, such tracking systems cannot correct for gross misalignments of the patient eye with the therapeutic laser. The design of the embodiments of the present invention can help a patient to properly fixate, and thus reduce the amount of eye movement during a surgical procedure. Perhaps more importantly, the embodiments of this system also allow a surgeon to identify if a patient is looking away beyond the limits of a tracking device, and thus stop the surgery if necessary. Because of the reduced eye movement that can result with proper fixation, better surgical results can be achieved.

The embodiments of the system of this invention can thus further comprise a wavefront analyzer for determining an ablation profile for the fixation target and/or also comprise a tracking system operable to track, and compensate for, movements of the fixation target to maintain a therapeutic laser beam aligned with a selected region of the fixation target for purposes of performing an ablation procedure on the fixation target. The ablation procedure can, for example, be based on the determined ablation profile. Embodiments of the method of the present invention can comprise providing such a tracking system and/or wavefront analyzer and determining the ablation profile. The wavefront analyzer and tracking system can be any such system as known to those familiar with the art.

Embodiments of the method and system of this invention thus provide various advantages over the prior art. The fixation light is contemplated to be a narrow, nearly collimated beam whose size and profile at the cornea are optimized to provide coarse and fine alignment to the doctor. The beam size and profile are also optimized such that the light source intensity and spot size on the patient's retina will not change appreciably with dioptric error of the eye, and such that the light image on the retina is minimally affected by, for example, a LASIK flap cut and the ongoing laser surgery. For the surgeon, coarse and fine alignment feedback features of the embodiments of this invention use a specular reflection that can incorporate a strategized beam profile, such that the monitored signal intensity is correlated to the distance between the corneal apex and the center of the fixation light beam. Likewise, the coarse and fine alignment features for the patient can incorporate a strategized beam profile, such that the beam intensity to the patient's retina is correlated to the distance between the corneal apex and the center of the fixation light beam. The patient and surgeon are thus able to make adjustments as required to obtain proper alignment and fixation. The coarse alignment light source may be of the same wavelength as the fine alignment light source for design efficiencies, or it may be a different wavelength to optimize the patient's ease of use (e.g., the light sources can be of different colors).

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide a means to align a reflective curved surface with a laser light source for the purposes of performing an ablation procedure on that surface.

What is claimed is:

1. A system for patient optical fixation, comprising:
   a light source operable to provide a fixation light beam;
   a filter optically coupled to the light source and operable to attenuate the fixation light beam to provide an apodized light beam, wherein the apodized light beam comprises a more attenuated portion and a less attenuated portion, and wherein the filter comprises a multi-component neutral density filter wherein at least one component comprises a filter section having an aperture for passing the less attenuated portion of the apodized light beam; and
   a viewer, operable to receive a reflected fine align beam and a reflected coarse align beam from a fixation target.

2. A system for patient optical fixation, comprising:
   a light source operable to provide a fixation light beam;
   a filter optically coupled to the light source and operable to attenuate the fixation light beam to provide an apodized light beam, wherein the apodized light beam comprises a more attenuated portion and a less attenuated portion;
   a viewer, operable to receive a reflected fine align beam and a reflected coarse align beam from a fixation target; and
   a set of focusing lenses operable to receive and focus the more attenuated portion of the apodized light beam to provide a patient coarse align light beam to aid a patient in achieving fixation on the less attenuated portion of the apodized light beam, wherein the patient coarse align light beam is an intermittent blinking patient coarse align light beam.

3. A system for patient optical fixation, comprising:
   a light source operable to provide a fixation light beam;
   a filter optically coupled to the light source and operable to attenuate the fixation light beam to provide an apodized light beam, wherein the apodized light beam comprises a more attenuated portion and a less attenuated portion; and
   a viewer, operable to receive a reflected fine align beam and a reflected coarse align beam from a fixation target, wherein the light source comprises;
      a fine align light source operable to provide a fine align light beam; and
      a coarse align light source operable to provide a coarse align light beam, wherein the fine align light source frequency is different from the frequency of the coarse align light source, and wherein the more attenuated portion of the apodized light beam comprises the filter-attenuated coarse align light beam, and the less attenuated portion of the apodized light beam comprises the filter-attenuated fine align light beam.

4. A method for patient optical fixation, comprising:
   providing a fixation light beam;
   attenuating the fixation light beam to provide an apodized light beam, wherein the apodized light beam comprises a more attenuated portion and a less attenuated portion;
   directing the apodized light beam onto a fixation target to produce a reflected fine align beam and a reflected coarse align beam;
   receiving the reflected fine align beam and the reflected coarse align beam at a viewer; and
   adjusting the fixation target position relative to the apodized light beam axis based on the reflected fine align beam and the reflected coarse align beam.

5. The method of claim 4, wherein the fixation light beam is provided by a light source, and wherein the light source is one of a laser, a light emitting diode and a laser diode.

6. The method of claim 4, wherein the fixation light beam is a nearly collimated beam of light.

7. The method of claim 4, wherein adjusting the fixation target position comprises aligning a fixation point on the fixation target with the apodized light beam axis.

8. The method of claim 4, wherein adjusting the fixation target position further comprises adjusting the fixation target position based on the difference in intensity between the reflected fine align beam and the reflected coarse align beam received at the viewer.

9. The method of claim 4, wherein the fixation light beam is attenuated at a filter.

10. The method of claim 9, wherein the filter is a neutral density ("ND") filter.

11. The method of claim 10, wherein the ND filter comprises:
an aperture through which a first portion of the fixation light beam can pass unattenuated by the ND filter to form the less attenuated portion of the apodized light beam; and
a filter region for attenuating a second portion of the fixation light beam to form the more attenuated portion of the apodized light beam.

12. The method of claim 11, wherein the aperture is a circular aperture, and wherein the less attenuated portion of the apodized light beam is approximately a central circular region of the apodized light beam and wherein the more attenuated portion of the apodized light beam is approximately an annular outer region of the apodized light beam, wherein the inner diameter of the more attenuated portion is approximately equal to the diameter of the less attenuated portion.

13. The method of claim 12, wherein the apodized light beam has a stepped intensity profile, with the less attenuated portion having a greater intensity than the more attenuated portion.

14. The method of claim 4, wherein the apodized light beam has a stepped intensity profile, with the less attenuated portion having a greater intensity than the more attenuated portion.

15. The method of claim 4, wherein the reflected fine align beam comprises the reflected less attenuated portion of the apodized light beam from the fixation target, and wherein the reflected coarse align beam comprises the reflected more attenuated portion of the apodized light beam from the fixation target.

16. The method of claim 15, wherein the fine align beam and the coarse align beam are each operable to provide an observer feedback to align the fixation light beam with a selected region of the fixation target, wherein the coarse align beam is operable to indicate to the observer a greater misalignment between the fixation light beam and the selected region, than can the fine align beam.

17. The method of claim 16, wherein the fixation target is a human eye, and wherein the selected region is a cornea of the human eye.

18. The method of claim 4, wherein the less attenuated portion of the apodized light beam has a spot size on the fixation target having a diameter of about 1 to 2 millimeters, and wherein the more attenuated portion of the apodized light beam has a spot size on the fixation target having an outer diameter of about 4 to 5 millimeters.

19. The method of claim 4, wherein the viewer is one of a surgical microscope and a video display.

20. The method of claim 4, further comprising aligning the fixation target with the apodized light beam axis.

21. The method of claim 20, further comprising directing a therapeutic laser beam onto the fixation target to ablate a selected region of the fixation target.

22. The method of claim 21, wherein the therapeutic laser beam and the fixation light beam have a common optical axis.

23. The method of claim 21, further comprising providing a tracking system operable to track, and compensate for, movements of the fixation target to maintain the therapeutic laser beam aligned with the selected region of the fixation target.

24. The method of claim 4, further comprising the step of determining an ablation profile for the fixation target.

25. The method of claim 4, further comprising the step of focusing the more attenuated portion of the apodized light beam to provide a patient coarse align light beam to aid a patient in achieving fixation on the less attenuated portion of the apodized light beam.

26. The method of claim 25, wherein the focusing the more attenuated portion of the apodized light beam further comprises intermittently blinking the patient coarse align light beam on and off.

* * * * *